United States Patent
Bhaskaran et al.

(10) Patent No.: US 9,241,937 B2
(45) Date of Patent: Jan. 26, 2016

(54) METHOD OF MANAGING UROLITHIASIS AND RELATED UROLOGICAL DISORDERS

(71) Applicant: INDUS BIOTECH PRIVATE LIMITED, Kondhwa, Pune, Maharashtra (IN)

(72) Inventors: Sunil Bhaskaran, Maharashtra (IN); Mohan Vishwaraman, Maharashtra (IN)

(73) Assignee: INDUS BIOTECH PRIVATE LIMITED, Kondhwa, Pune, Maharashtra (IN)

( * ) Notice: Subject to any disclaimer, the term of this patent is extended or adjusted under 35 U.S.C. 154(b) by 0 days.

(21) Appl. No.: 14/439,657

(22) PCT Filed: Oct. 31, 2013

(86) PCT No.: PCT/IB2013/059821
§ 371 (c)(1),
(2) Date: Apr. 29, 2015

(87) PCT Pub. No.: WO2014/068516
PCT Pub. Date: May 8, 2014

(65) Prior Publication Data
US 2015/0283126 A1    Oct. 8, 2015

(30) Foreign Application Priority Data
Nov. 2, 2012 (IN) .......................... 3199/MUM/2012

(51) Int. Cl.
*A61K 31/455* (2006.01)
*A61K 31/198* (2006.01)

(52) U.S. Cl.
CPC ............. *A61K 31/455* (2013.01); *A61K 31/198* (2013.01)

(58) Field of Classification Search
None
See application file for complete search history.

(56) References Cited

U.S. PATENT DOCUMENTS

2008/0221173 A1*  9/2008  Bhaskaran ........... A61K 31/198
                                                  514/356

OTHER PUBLICATIONS

Laroubi, A. et al. "Prophylaxis Effect of Trigonella foenum graecum L. Seeds on Renal Stone Formation in Rats.", Phytotherapy Research, vol. 21, p. 921-925. Published online Jun. 20, 2007.
Abd-El Mawla, A.M.A. et al. "Elicitation of Trigoneline and 4-Hydroxyisoeucine with Hypoglycemic Activity in Cell Suspension Cultures of Trigonella foenum graecum L.". The Open Conference Proceedings Journal, 2011, 2, 8-87.
Ahsan, S.K. et al "Effect of Trigonella Foenum-Graecum and Ammi Majus on Calcium Oxalate Urolithiasis in Rats". Journal of Ethnopharmacology, vol. 26, p. 249-254. 1989.
Indian Traditional Knowledge Digital Library (TKDL). Abstract MH3/446A, Muheet-e Azam, vol. I (19th Centuary AD), Matba Nizami, Kanpur, 1896 AD "Sharbat-e-Biskhapra/handaquqa".
Indian Traditional Knowledge Digital Library (TKDL). Abstract KU1C/316, Ikseer Azam, vol. III (19th Centuary AD), Munshi Nawal Kishore, Lucknow 1917 AD "Dawa Barae Hissat".
International Search Report (PCT/132013/059821) dated Dec. 2, 2014, 24 pages.

* cited by examiner

*Primary Examiner* — Yevegeny Valenrod
(74) *Attorney, Agent, or Firm* — Blakely Sokoloff Taylor & Zafman LLP (57) ABSTRACT

The present disclosure relates to a method of managing urolithiasis or related urological disorders in a subject in need thereof, using pharmaceutical composition comprising trigonelline or its derivative(s) and 4-hydroxyisoleucine or its derivative(s), optionally along with excipient(s).

10 Claims, 2 Drawing Sheets

METHOD OF MANAGING UROLITHIASIS AND RELATED UROLOGICAL DISORDERS

TECHNICAL FIELD

The present disclosure relates to management of urolithiasis and related urological disorders. In particular, the present disclosure relates to the management of urolithiasis and related urological disorders such as hyperoxaluria, hypocitraturia, hyperuricosuria, kidney disorders, nephrolithiasis, ureterolithiasis, cystolithiasis, obstruction in urine output, creatinine clearance and recurrence of stone formation etc, by administration of a pharmaceutical composition comprising trigonelline or its derivative(s) and 4-hydroxyisoleucine or its derivative(s), optionally along with excipients(s).

BACKGROUND AND PRIOR ART OF THE DISCLOSURE

Urolithiasis is a process of forming stones anywhere in urinary tract i.e. in the kidney, bladder, and/or ureters. Kidney stones are among the most common and painful disorders of the urinary tract. The term nephrolithiasis (or "renal calculus") refers to stones located in the kidney. Kidney stones affect up to about 5% of the population, with a lifetime risk of passing a kidney stone of about 8-10%.

Urolithiasis takes place with nucleation, aggregation and retention of salts in urine wherein salts bind to the colloid matrices in the kidney and urinary tract. In this process, aggregates of tiny crystals of urinary salts are formed, named as kidney stones or renal calculi. Kidney stones or renal calculi can be classified according to the specific type of crystals they contain such as calcium oxalate, calcium phosphate, struvite, uric acid and cysteine. Some of the factors causing renal calculi are super saturation of urine with stone forming salts such as Calcium oxalate, calcium phosphate, uric acid, nutritional and environmental factors like dehydration, excess animal protein in diet, decrease in urinary pH, increase in the crystalloid level and/or fall in colloid level, change in urinary magnesium/calcium ratio, infection of the urinary tract, urinary stasis, decreased urinary output of citrate, vitamin deficiency, hyperparathyroidism and prolonged immobilization. These metabolic abnormalities are described by different terminologies such as hypercalciurea, hypocitraturia, hyperoxaluria, hyperuricosuria etc. When urine gets super saturated with stone forming salt ions such as calcium oxalate, they spontaneously join together to form solid crystals. The tiny crystals stick together forming large aggregates which get retained in the kidney and continue to grow larger. If the stones have grown to a critical size such as 5-10 mm in diameter then passage of stones through kidneys to ureters may get obstructed leading to pain and inflammation.

Physiological effect of urolithiasis depends on the size and position of the calculus. Presence of calculi can produce obstruction in the kidney leading to infection, metaplasia and parenchymal ischaemia. In case of renal calculi of one of the kidneys, compensatory hypertrophy due to over exertion can be induced in the other healthy kidney as well.

The most common complication is kidney stone recurrence. People who have passed one kidney stone have a 60-80% likelihood of having another one at some point in their life. Preventing recurrence is largely specific to the type of stone (e.g., calcium oxalate, calcium phosphate, cystine, struvite [magnesium ammonium phosphate], and uric acid stones). However, even when the stone cannot be retrieved, urine pH and 24-hour urine assessment for various parameters provide information about stone-forming factors that can guide prevention of recurrence.

Treatment for urolithiasis is decided on the basis of ultrasound scanning of the kidneys and urinary tract and analyzing the size and location of the calculi. Small sized calculi are tried for treatment with plenty of water intakes to flush out the calculi from the urinary system. This is usually supported with prescription of diuretics such as thiazides, potassium citrate etc, for increasing urination and pain killers to relieve the discomfort associated with passing out of the calculus. In USA, about 80% of renal calculi fall in this segment. Remaining 20% diagnosed with larger calculi are treated using extracorporeal shock wave lithotripsy (ESWL), percutaneous nephrolithotomy or uteroscopy. Due to the difficulty in flushing out larger sized calculi, ESWL is used to break it down so that they can be flushed out in the urine. However, ESWL is associated with side effects like moderate pain, blood in urine, bruising of back or abdomen by the sound waves, bleeding around the kidney and adjacent organs etc. Further, ESWL is not very successful in removal of large stones which are subsequently removed by surgery.

Countries of Middle East, North Africa, the Mediterranean Regions, North Western state of India, Southern State of USA and areas around the great lakes have been listed as high-risk areas and termed as the 'stone belt' regions of the world, where large numbers of patients suffer from renal calculi. In these countries, diagnosis and prevention of renal calculi are not taken seriously. Due to fear of surgical procedures and side effects of lithotripsy, many patients refuse to undergo these procedures. Instead they try to survive by using excessive pain killers.

Surgical procedures though effective in treatment involve high cost and lead to other side effects of urinary tract infection. Due to the limitations associated with clinical procedures to remove renal calculi, there is growing need for drugs which can help in complete removal of renal calculi. Hence there is need to develop drugs which will reduce the cost of management of the disorder and provide health to the patient by aggressive prevention of stone formation. The instant disclosure aims to address these concerns of the prior art.

Bhaskaran et al (US2008/0221173A1) discloses a pharmaceutical composition having dopaminergic activity and other related pharmaceutical activities comprising trigonelline or its derivative(s) and 4-Hydroxyisoleucine or its derivative(s), optionally along with excipients(s), and a process of preparing the composition. It also discloses a method of treating side effects caused by dopamine receptor antagonists. However this document does not suggest or teach use of said composition in managing urolithiasis and related urological disorders such as hyperoxaluria, hypocitraturia, hyperuricosuria, kidney disorders, ureterolithiasis, and obstruction in urine output, creatinine clearance and recurrence of stone formation.

STATEMENT OF THE DISCLOSURE

Accordingly, the present disclosure relates to a method of managing urolithiasis and related urological disorders, said method comprising act of administering composition comprising trigonelline or its derivative(s) and 4-hydroxyisoleucine or its derivative(s), optionally along with pharmaceutical excipient, to subject in need thereof.

BRIEF DESCRIPTION OF THE ACCOMPANYING FIGURES

In order that the disclosure may be readily understood and put into practical effect, reference will now be made to exemplary embodiments as illustrated with reference to the accompanying figures. The figure together with a detailed description below, are incorporated in and form part of the specification, and serve to further illustrate the embodiments and explain various principles and advantages, in accordance with the present disclosure, wherein.

DETAILED DESCRIPTION OF THE DISCLOSURE

The present disclosure relates to a method of managing urolithiasis and related urological disorders, said method comprising act of administering composition comprising trigonelline or its derivative(s) and 4-hydroxyisoleucine or its derivative(s), optionally along with pharmaceutical excipient, to subject in need thereof.

In an embodiment of the present disclosure, the urolithiasis is selected from a group comprising nephrolithiasis, ureterolithiasis and cystolithiasis or any combination thereof.

In another embodiment of the present disclosure, the related urological disorder is selected from a group comprising hyperoxaluria, hypocitraturia, hyperuricosuria, accumulation of calcium crystals in renal tubule, low creatinine clearance rate, high BUN, serum creatinine and serum uric acid level, low urinary pH, recurrence of calculi and other kidney disorder or any combination thereof.

In yet another embodiment of the present disclosure, the trigonelline or its derivative(s) is at concentration ranging from about 30% w/w to about 90% w/w; the 4-hydroxyisoleucine or its derivative(s) is at concentration ranging from about 10% w/w to about 30% w/w; and the pharmaceutical excipient is at concentration ranging from about 0.5% w/w to about 30% w/w.

In still another embodiment of the present disclosure, the derivative(s) of trigonelline is selected from group comprising hydrochloride derivatives, acetate derivatives, citrate derivatives, benzoate derivatives, salt derivatives and acid derivatives, preferably hydrochloride derivatives.

In still another embodiment of the present disclosure, the derivative(s) of 4-hydroxyisoleucine is selected from group comprising hydrochloride derivatives, acetate derivatives, citrate derivatives, benzoate derivatives, salt derivatives and acid derivatives, preferably hydrochloride derivatives.

In still another embodiment of the present disclosure, the pharmaceutical excipient is selected from group comprising gums, granulating agents, binders, lubricants, disintegrating agents, sweetening agents, additives, solvents, glidants, anti-adherents, anti-static agents, surfactants, anti-oxidants, surfactants, viscocity enhancers, plant cellulosic material coloring agents, flavoring agents, coating agents, plasticizers, preservatives, suspending agents, emulsifying agents, antistatic agents and spheronization agents or any combination thereof.

In still another embodiment of the present disclosure, the composition is formulated into dosage forms selected from group comprising solid oral formulation, liquid oral formulation, parenteral formulation, phytoceutical, nutraceutical and food stuff or any combinations thereof.

In still another embodiment of the present disclosure, the composition is administered at dose ranging from about 1 mg/kg to about 100 mg/kg, preferably ranging from about 1 mg/kg to about 25 mg/kg of body weight of said subject per day.

In still another embodiment of the present disclosure, the subject is a mammal, including human being.

The present disclosure discloses a method of management, cure and prevention of recurrent urolithiasis and related disorders using a composition of trigonelline and 4-hydroxyisoleucine or derivatives thereof. Trigonelline is present in many natural sources like coffee beans, fenugreek, green peas, soybeans etc. It is widely known for its hypoglycemic action and has hypolipidemic, neuroprotective, antimigraine, sedative, memory-improving, antibacterial, antiviral, and anti-tumor activities. It has been shown to reduce diabetic auditory neuropathy and platelet aggregation. 4-hydroxyisoleucine is also widely investigated for its insulinotropic and antidiabetic properties. Both these compounds are commercially available as reference standards.

In an embodiment of the present disclosure, urolithiasis and related urological disorders involve hyperoxaluria, hypocitraturia, hyperuricosuria, kidney disorders and recurrence of stone formation etc.

In another embodiment of the present disclosure, the trigonelline is obtained from plant or animal source. The trigonelline is obtained from *Trigonella foenumgraecum* and *Coffea arabica*. The derivative(s) of trigonelline are selected from group comprising hydrochloride derivatives, acetate derivatives, citrate derivatives, benzoate derivatives, salt derivatives and acid derivatives, preferably hydrochloride derivatives.

In still yet another embodiment of the present disclosure, the 4-hydroxyisoleucine is obtained from plant source, preferably *Trigonella foenum-graecum*. The derivative(s) of 4-hydroxyisoleucine are selected from group comprising hydrochloride derivatives, acetate derivatives, citrate derivatives, benzoate derivatives, salt derivatives and acid derivatives, preferably hydrochloride derivatives.

In still another embodiment of the present disclosure, the excipients(s) are selected from group comprising granulating agents, binding agents, lubricating agents, disintegrating agents, sweetening agents, glidants, anti-adherents, antistatic agents, surfactants, anti-oxidants, gums, coating agents, coloring agents, flavouring agents, plasticizers, preservatives, suspending agents, emulsifying agents and spheronization agents.

In still another embodiment of the present disclosure, the composition is formulated into dosage forms selected from group of solid oral formulations, liquid oral formulations, parenteral formulations, phytoceuticals, nutraceuticals and food stuffs or any combination thereof. Depending on the route of administration, different excipients/carriers are used.

In still another embodiment of the present disclosure, the solid oral formulation is selected from group comprising tablet, capsule, troche, lozenge, dispersible powder, dispersible granule or any combination thereof.

In still another embodiment of the present disclosure, the liquid oral formulation is selected from group comprising aqueous or oily suspension, emulsion, drops, emulsion in hard or soft gel capsule, syrup, elixir or any combination thereof.

In still another embodiment of the present disclosure, the parenteral formulation is selected from group comprising intravenous injection, intramuscular injection, intramuscular depot, subcutaneous injection, percutaneous injection or any combination thereof.

In still another embodiment of the present disclosure, managing urolithiasis and related urological disorders involves reducing the cost of management of the disease condition, providing health to the patient by prevention of stone formation, complete removal of calculi to avoid surgical procedures, and provide relief to the patient from symptoms of kidney stones—renal colic, hematuria etc. and side effects such as urinary tract infection, chronic kidney disease, kidney failure and recurrences of stone formation.

In still another embodiment of the present disclosure, the term "instant composition" includes a pharmaceutical composition containing trigonelline or its derivative(s) at concentration from about 30% to about 90% and 4-hydroxyisoleucine or its derivative(s) at concentration from about 10% to about 30%, optionally along with excipients(s).

In still another embodiment of the present disclosure, the term "managing" or "management" includes preventing, treating, curing a disease condition or disorder or ill effects or side effects. The term also encompasses maintenance of the optimum state and prevention of the further progress in the disease condition or disorder or ill effects or side effects. Hence, the term indicates preventing the disease condition, curing the disease condition and preventing the recurrence of the disease condition.

In still another embodiment of the present disclosure, hyperoxaluria is excess Oxalate in the Urine. Oxalate is the most common stone-forming compound. Excessive oxalate in the urine is responsible for up to 60% of calcium stones and is a more common cause of stones than excess calcium in the urine. Hyperoxaluria can be either primary or secondary. Excretion of oxalate occurs primarily by the kidneys via glomerular filtration and tubular secretion. As oxalate can bind with calcium in the kidney, increased urinary oxalate excretion (hyperoxaluria) leads to urinary CaOx supersaturation, resulting in the formation and putative retention of CaOx crystals in renal tissue.

In still another embodiment of the present disclosure, hypocitraturia is low urine levels of Citrate. Citrate is the main substance in the body that is responsible for removing excess calcium. It also blocks the process that turns calcium crystals into stones. It is recognized as an important natural inhibitor of calcium-containing renal stone formation, citrate may reduce urinary calcium saturation by forming a soluble complex with calcium and inhibiting growth of calcium phosphate and calcium oxalate crystals. Hypocitraturia increases the risk for calcium stones, uric acid stones. This condition most likely contributes to about a third of all kidney stones. Hypocitraturia is predominantly of dietary origin. Hypocitraturia contributes to calcium stone formation by enhancing urinary calcium saturation through reduced formation of citrate-calcium complex and by promoting spontaneous nucleation and crystal growth through reduced inhibitor activity.

In still another embodiment of the present disclosure, hyperuricosuria is excess of Uric Acid in urine. It plays a role in stone generation in some calcium oxalate stone formers. Hyperuricosuria promotes the founation of sodium and potassium urate crystals, both of which may serve as a heterogenous nidus for the nucleation of other crystals such as calcium oxalate.

In still another embodiment of the present disclosure, the instant composition is formulated into a suitable dosage formulation for managing urolithiasis and related urological disorders, using a dose ranging from about 1 mg/kg to about 100 mg/kg of body weight of subject per day, preferably ranging from about 1 mg/kg to about 25 mg/kg of body weight of subject per day, or a dosage of about 300 mg twice a day or any suitable dosage range that a person skilled in the art will know to arrive at.

The instant disclosure aims at reducing the cost of management of the disease and related disorders providing health to the patient by aggressive prevention of stone formation, complete removal of calculi to avoid surgical procedures and providing relief from symptoms of kidney stones—renal colic, hematuria etc. and side effects such as urinary tract infection, chronic kidney disease, kidney failure and recurrences of stone formation.

The instant disclosure is further elaborated with the help of following examples. However, these examples should not be construed to limit the scope of the disclosure.

EXAMPLES

Example 1

Formulation of the Instant Composition

The instant composition can be obtained and subsequently formulated by various techniques available in the art. Two such techniques have been provided below.

Example 1.1

About 1000 grams of fenugreek seeds having moisture content less than about 5% are flaked in a roller flaker to a thickness of about 2 mm. The flaked material is stalked in a column having a bed height of about 300 mm. About 5 liters of hexane is passed through the layer of fenugreek and the eluent collected from the bottom is recycled through the fenugreek layer for a period of about 10 hrs at about 35° C. After about 10 hrs the fenugreek layer is drained free of hexane. Solvent mixture (about 8 liters) comprising of ethyl alcohol and water in the ratio of about 3.5:1 is passed through the layer for a period of about 8 hrs at about 35° C. by recycling the eluent. After about 8 hrs the fenugreek bed is drained free of extracts and all the collected extracts are concentrated to semisolid mass under vacuum at about 50° C.

The concentrated mass is redissolved in about 5 liters of deionised water to get a clear solution. The clear aqueous solution is passed through a column containing about 400 ml of strong acid cation exchange gel type resin for about 2 hrs. TLC screening for the absence of trigonelline is checked on the column eluent using a system consisting of n-Butanol: Acetic acid:Water in the ratio of about 12:8:4 as the mobile phase on silica Gel precoated plate F254 (1.05554.007) and observed under UV 254 nm. After saturation of the column the resin bed is washed free of colors and adhering impurities using about 4 liters of deionised water. The column is desorbed using 800 ml of aqueous ammonia of about 5N strength at a rate of about 400 ml per hour. The mixture eluted out is concentrated under vacuum at about 45° C. to a semisolid mass.

The dried mass is redissolved in about 150 ml of deionised water and filtered free of insoluble impurities. The solution is concentrated under vacuum at about 50° C. to a solid content of about 20% and spray dried in a co-current indirect hot air spray dryer under following conditions.

Inlet temperature: about 160° C.
Outlet temperature: about 80° C.
Atomizer RPM: about 12000

The yield is about 10 gms. HPLC showed about 35% Trigonelline & about 18% 4-Hydroxyisoleucine amino acid.

Example 1.2

About 1000 grams of green *Coffea Arabica* seeds having moisture content less than about 15% are flaked in a roller flaker to a thickness of about 2 mm. The flaked material is stalked in a column having a bed height of about 500 mm. Solvent mixture (about 8 liters) comprising of water and ethyl alcohol in the ratio of about 9:1 is passed through the layer for a period of about 8 hrs at about 35° C. by recycling the eluent. After about 8 hrs the *Coffea arabica* bed is drained free of extracts and all the collected extracts are concentrated to semisolid mass under vacuum at about 50° C.

The concentrated mass is redissolved in about 5 liters of deionised water to get a clear solution. The clear aqueous solution is passed through a column containing about 400 ml of strong acid cation exchange Gel type resin for about 2 hrs. TLC screening for the absence of trigonelline is checked on the column eluent using a system consisting of n-Butanol: Acetic acid:Water in the ratio of about 12:8:4 as the mobile phase on silica Gel precoated plate F254 (1.05554.007) and observed under UV 254 nm. After saturation of the column the resin bed is washed free of colors and adhering impurities using about 4 liters of deionised water. The column is desorbed using about 800 ml of aqueous ammonia of about 5N strength at a rate of about 400 ml per hour. The mixture eluted out is concentrated under vacuum at about 45° C. to a semi-solid mass.

The dried mass is redissolved in about 150 ml of deionised water and filtered free of insoluble impurities. The solution is concentrated under vacuum at about 50° C. to a solid content of about 20% and spray dried in a co-current indirect hot air spray dryer under following conditions.
Inlet temperature: about 160° C.
Outlet temperature: about 80° C.
Atomizer RPM: about 12000

The yield is about 5 grams. HPLC showed about 60% trigonelline & remaining amino acids.

The above material is redissolved in about 200 ml of ethyl alcohol, filtered through 41 Whatmann filter paper and cooled to about 0° C. A dry stream of hydrogen chloride gas is passed through this to precipitate the trigonelline hydrochloride. The precipitate is filtered out on filter paper and washed with cold ethyl alcohol and dried under vacuum at about 60° C.

Example 2

Activity of the Instant Composition in Ethylene Glycol Induced Urolithiasis in Rats Urolithiasis is induced in male wistar rats weighing about 150-250 g by administering Ethylene Glycol (EG) and Ammonium Chloride (0.75% v/v EG+1% w/v AC) orally in water for about 3 days and only Ethylene Glycol (0.75% v/v EG) until about day 28.

EG induced urolithiasis model is well validated and clinically relevant. EG metabolizes into CaOx monohydrate (COM) and produces renal mitochondrial toxicity similar to clinical CaOx renal calculi. (McMartin and Wallace, 2005). In the present study, therapeutic activity of instant composition is evaluated on renal calculi induced by EG+AC in male rats. AC is administered to rats along with EG to accelerate lithiasis.

Animals are divided into four groups containing about six animals in each group. All animals are treated as per respective groups:

Group 1: Normal Control: Saline (10 ml/kg).

Group 2: Disease Control: 0.75% v/v Ethylene Glycol (EG)+t 1% w/v Ammonium Chloride (AC) for about 3 days and only Ethylene Glycol (0.75% v/v) until about day 28.

Group 3: Instant composition: About 30 mg/kg of instant composition (i.e. the composition as stated in Example 1.1 comprising 35% Trigonelline & 18% 4-Hydroxyisoleucine amino acid)+(EG 0.75% v/v+AC 1% w/v) for about 3 days and only Ethylene Glycol (0.75% v/v) until about day 28.

Group 4: Instant composition: About 60 mg/kg of instant composition (i.e. 35% Trigonelline & 18% 4-Hydroxyisoleucine amino acid)+(EG t 0.75% v/v+AC 1% w/v) for about 3 days and only ethylene Glycol (0.75% v/v) until about day 28.

Treatment with instant composition (about 30 mg/kg and about 60 mg/kg) is initiated on about day 15 and continued until about day 28. Analyses are carried out to monitor the kidney function. Urine samples over about 24 hour period (24-h) are collected on $0^{th}$ $14^{th}$ and $28^{th}$ day respectively. Serum is collected after about $28^{th}$ day. Animals are sacrificed after $28^{th}$ day. Kidneys are removed for histological study.

Example 2.1

Hyperoxaluria is defined as urinary excretion of oxalate in excess. It is a significant diagnostic marker for calcium oxalates urolithiasis because increased urinary oxalate promotes calcium oxalate crystallization and stone formation.

The oxalate in urine is estimated by the following procedure.

1. About 1 ml of urine is acidified using concentrated $HNO_3$ to solubilize the crystals and then adjusted to a pH of about 7 (green color) by NaOH in the presence of bromothymol blue.
2. The oxalate in the samples is precipitated by adding about 2 ml of saturated $CaSO_4$ and about 14 ml of pure ethanol over about 18 h.
3. The samples are centrifuged at about 2500 rpm for about 10 min and precipitate of calcium oxalate obtained is separated and washed with dilute ammonia solution.
4. The precipitate obtained is solubilized in about 10 ml of water acidified by about 2 ml of concentrated $H_2SO_4$.
5. The samples are titrated with a solution of about 0.01N $KMnO_4$ at temperature ranging from about 60° C. to about 70° C. and the oxalate is calculated.

Calculation: 1.0 ml of 0.01 N $KMnO_4$=0.45 mg of anhydrous oxalic acid

The effect of the instant composition on 24-h urine oxalate level for a period of about 28 days is studied as indicated in Example 2 above. The results obtained are tabulated in Table 1 wherein n=6; the data is represented as mean±SEM. (n=6), Data is analyzed by separate Two-Way ANOVA followed by Bonferroni Posttest for each parameter. ns—not significant, ####$p<0.001$ as compared with Normal group,  $p<0.01$, *$p<0.001$ as compared with (EG+AC) group on respective days.

TABLE 1

Effect of Instant composition on 24-h urine oxalate level 24-h Urine Oxalate (mg/ml)

| Treatment | Normal Control | Disease Control | Ethylene Glycol + Instant composition (about 30 mg/kg) Treatment initiated on Day 15 | Ethylene Glycol + Instant composition (about 60 mg/kg) Treatment initiated on Day 15 |
|---|---|---|---|---|
| Baseline i.e. Day 0 | 0.54 ± 0.02 | 0.53 ± 0.04 | 0.63 ± 0.07 | 0.61 ± 0.03 |
| Day-14 | 0.47 ± 0.05 | 4.1 ± 0.29### | 3.72 ± 0.14 | 3.76 ± 0.11 |
| Day-21 | 0.52 ± 0.02 | 4.8 ± 0.25### | 4.12 ± 0.26*** | 3.08 ± 0.09*** |
| Day-28 | 0.53 ± 0.06 | 5.96 ± 0.29### | 4.27 ± 0.24*** | 2.41 ± 0.17*** |

As shown in Table 1, there is significant increase in 24-h urine oxalate level in the disease control group when compared to the normal control group on day 14. The instant composition (about 60 mg/kg) significantly reversed urine oxalate increment as compared to disease control group on day 21 and onwards as seen in Table 1. Thus, by preventing urine oxalate increment, instant composition helps to prevent super saturation of urinary Calcium Oxalate which ultimately reduces the obstructions of urinary output. This aspect helps in managing urolithiasis and other related urological disorders.

Example 2.2

Hypocitraturia, a low amount of citrate in the urine, is an important factor for kidney stone formation. It also plays a role in uric acid solubility and uric acid stone formation.

The amount of citrate in urine sample is estimated as follows:

1. In about 25 ml glass stoppered tube, marked as 'B', about 2 ml of water and about 2 ml of about 10% TCA are added.
2. In a centrifuge tube, the following are taken: about 1 ml of urine sample, about 3 ml of water and about 4 ml of 10% TCA. The contents are mixed and centrifuged if necessary. About 4 ml (about 0.5 ml urine) of supernatant is transferred into about 25 ml glass stoppered tube marked as 'T'.
3. In about 25 ml glass stoppered tube, marked as 'S', about 1 ml of working standard solution, about 1 ml water and about 2 ml of about 10% TCA are added.
4. To all the tubes, about 1 ml of about 9 N $H_2SO_4$ is added followed by about 0.25 ml of about 40% metaphosphoric acid, mixing after each addition.
5. The tubes are kept in ice water taken in a beaker, at temperature below about 10° C.
6. After about 5 min, to each tube, about 0.5 ml of about 2 M KBr and about 1.5 ml of about 6.5% KMnO4 are added, mixed and left in the ice-water bath for about 10 min. This is the principle reaction where citric acid is oxidized to pentabromoacetone (PBA).
7. The KMnO4 is then decolorized in each tube with drop wise addition of about 6% $H_2O_2$.
8. The tubes are removed and about 5 ml of petroleum ether is added to each tube.
9. The tubes are stoppered and shaken manually for about 2 min for extraction of the PBA into the petroleum ether. The layers are allowed to separate.
10. About 4 ml of the petroleum ether layer are transferred quickly into about 15 ml glass stoppered centrifuge tubes.
11. Thiourea-borax (about 6 ml) solution is added to each tube, stoppered and the contents are shaken for about 2 min.
12. A golden yellow color is developed in the aqueous layer in test and standard tubes. The blank is clear.
13. The tubes are centrifuged for about 5 min.
14. The top petroleum ether from each tube is aspirated.
15. The absorbance of the colored aqueous layers is read in a spectrophotometer at about 445 nm.

Calculation:

µg of citric acid in 0.5 ml of urine=(Absorbance of test)/(Absorbance of standard)×100

The effect of the instant composition on 24-h urine citrate level for a period of about 28 days is studied as indicated in Example 2 above. The results obtained are tabulated in Table 2 wherein n=6; the data is represented as mean±SEM. (n=6), Data is analyzed by separate Two-Way ANOVA followed by Bonferroni Posttest for each parameter. ns—not significant, ###$p<0.001$ as compared with Normal group,  $p<0.01$, *$p<0.001$ as compared with (EG+AC) group on respective days.

TABLE 2

Effect of Instant composition on 24-h urine citrate level 24-h Urine Citrate (mg/ml)

| Treatment | Normal Control | Disease Control | Ethylene Glycol + Instant composition (about 30 mg/kg) Treatment initiated on Day 15 | Ethylene Glycol + Instant composition (about 60 mg/kg) Treatment initiated on Day 15 |
|---|---|---|---|---|
| Baseline | 12.27 ± 0.41 | 12.78 ± 0.16 | 13.37 ± 0.27 | 12.76 ± 0.65 |
| Day-14 | 12.48 ± 0.31 | 9.46 ± 0.26### | 8.67 ± 0.51 | 9.33 ± 0.15 |

TABLE 2-continued

Effect of Instant composition on 24-h urine citrate level

| | | | 24-h Urine Citrate (mg/ml) | |
| --- | --- | --- | --- | --- |
| Treatment | Normal Control | Disease Control | Ethylene Glycol + Instant composition (about 30 mg/kg) Treatment initiated on Day 15 | Ethylene Glycol + Instant composition (about 60 mg/kg) Treatment initiated on Day 15 |
| Day-21 | 12.44 ± 0.07 | 8.33 ± 0.33### | 9.49 ± 0.70 | 10.12 ± 0.32** |
| Day-28 | 12.92 ± 0.46 | 7.68 ± 0.31### | 8.88 ± 0.70 | 10.20 ± 0.08*** |

As shown in Table 2, there is significant decrease in 24-h urine citrate level in the disease control group when compared to the normal control group on day 14. The instant composition (about 60 mg/kg) significantly reversed urine citrate decline as compared to disease control group on day 21 and onwards as seen in Table 2. Thus by preventing further decline in urine citrate level, instant composition decreases the risk of Calcium, Uric acid stone formation. This aspect helps in managing urolithiasis and other related urological disorders.

Example 2.3

Accumulation of calcium crystals in renal tubule causes obstruction in urine output. The effect of the instant composition on 24-h urine output for a period of about 28 days is studied as indicated in Example 2 above. The results obtained are tabulated in Table 3 wherein n=6; the data is represented as mean±SEM. (n=6), Data is analyzed by separate Two-Way ANOVA followed by Bonferroni Posttest for each parameter. ns—not significant, ####p<0.001 as compared with Normal group,  p<0.01, *p<0.001 as compared with (EG+AC) group on respective days.

obstructions of urine output and preventing further saturation of urinary salts such as oxalate, citrate, etc. This aspect helps in managing urolithiasis and other related disorders.

Example 2.4

Creatinine clearance rate (CCr or CrCl) is the volume of blood plasma that is cleared of creatinine per unit time and is a useful measure for approximating the glomerular filtration rate (GFR). Creatinine clearance exceeds GFR due to creatinine secretion. Creatinine clearance rate is calculated by following formula:

$$CrCl = (uCr \times uV)/(sCr \times 1440)$$

Annotation

Where: CrCl is Creatinine clearance in ml/min,
uCr is Urine Creatinine in mg/dl,
sCr is Serum Creatinine in mg/dl,
uV is 24 hour urine volume in ml and
1440 represents number of minutes in 24 hours The effect of the instant composition on 24-h creatinine clearance for a period of about 28 days is studied as indicated in Example 2 above. The results obtained are tabulated in

TABLE 3

Effect of Instant composition on 24-h urine output

| | | | 24-h Urine output (ml/day) | |
| --- | --- | --- | --- | --- |
| Treatment | Normal Control | Disease Control | Ethylene Glycol + Instant composition (about 30 mg/kg) Treatment initiated on Day 15 | Ethylene Glycol + Instant composition (about 60 mg/kg) Treatment initiated on Day 15 |
| Baseline | 12.27 ± 0.41 | 12.78 ± 0.16 | 13.37 ± 0.27 | 12.76 ± 0.65 |
| Day 14 | 12.48 ± 0.31 | 9.46 ± 0.26### | 8.67 ± 0.51 | 9.33 ± 0.15 |
| Day 21 | 12.44 ± 0.07 | t8.33 ± 0.33#### | 9.49 ± 0.70 | 10.12 ± 0.32** |
| Day 28 | 12.92 ± 0.46 | 7.68 ± 0.31#### | 8.88 ± 0.70 | 10.20 ± 0.08*** |

As shown in Table 3, there is significant decrease in 24-h urine output in the disease control group when compared to the normal control group on day 14. The instant composition (about 60 mg/kg) significantly reversed urine output decline as compared to disease control group on day 21 and onwards as seen in Table 3. The instant composition shows removing Table 4 wherein n=6; the data is represented as mean±SEM. (n=6), Data is analyzed by separate Two-Way ANOVA followed by Bonferroni Posttest for each parameter. ns—not significant, ####p<0.001 as compared with Normal group,  p<0.01, *p<0.001 as compared with (EG+AC) group on respective days.

TABLE 4

Effect of Instant composition on 24-h Creatinine clearance

| Treatment | Day-28 | | | |
|---|---|---|---|---|
| | Normal Control | Disease Control | Ethylene Glycol + Instant composition (about 30 mg/kg) Treatment initiated on Day 15 | Ethylene Glycol + Instant composition (about 60 mg/kg) Treatment initiated on Day 15 |
| Urine Creatinine | 62.56 ± 0.87 | 29.70 ± 0.22### | 31.34 ± 1.09 | 39.15 ± 0.39*** |
| 24-h Urine output | 12.92 ± 0.46 | 7.68 ± 0.31### | 8.88 ± 0.70 | 10.20 ± 0.08*** |
| Serum Creatinine | 1.32 ± 0.15 | 3.32 ± 0.60### | 3.10 ± 0.08 | 1.93 ± 0.95 *** |
| Creatinine Clearance | 0.43 ± 0.05 | 0.05 ± 0.01### | 0.02 ± 0.01 | 0.19 ± 0.10 *** |

As shown in Table 4, there is significant decrease in 24-h urine Creatinine clearance rate in the disease control group when compared to the normal control group on day 28. The instant composition (about 60 mg/kg) significantly reversed Creatinine clearance rate decline as compared to disease control group as seen in Table 4. The instant composition enhances glomerular filtration rate which helps in reducing the obstructions of urine, increasing urine output and maintaining oxalate, citrate, uric acid levels and preventing further saturation of urinary salts. Glomerular filtration rate (GFR) describes the flow rate of filtered fluid through the kidney. Creatinine clearance rate (CCr or CrCl) is the volume of blood plasma that is cleared of creatinine per unit time and is a useful measure for approximating the GFR. Creatinine clearance exceeds GFR due to creatinine secretion, which can be blocked by cimetidine. Glomerular filtration rate (GFR) is equal to the clearance rate when any solute is freely filtered and is neither reabsorbed nor secreted by the kidneys. The rate therefore measured is the quantity of the substance in the urine that originated from a calculable volume of blood. This example shows that the instant composition (about 60 mg/kg) significantly reverses creatinine clearance rate decline as compared to disease control group. Thus the instant composition is ultimately capable of maintaining GFR and in reducing the obstructions of urine preventing further saturation of urinary salts. This aspect helps in managing urolithiasis and other related urological disorders.

Example 2.5

Blood urea nitrogen (BUN) is a toxic metabolite which gets accumulated into the blood in diseased state. The levels of BUN and serum creatinine are screening tests of renal function. Since they are handled primarily by glomerular filtration with little or no renal regulation or adaptation in the course of declining renal function, they essentially reflect GFR.

The procedure for estimating blood urea nitrogen in serum by Accurex Autozyme kit is as follows:

A working solution is prepared by mixing an enzyme vial in about 50 ml diluting fluid. Working reagents are stable till the expiry date stated on the bottle label, when stored at room temperature (<30° C.). About 1 ml of the working reagent is pipetted in to all tubes. The tubes are labeled and kept ready for addition of specimen (about 10 µl).

1. Blood is withdrawn from the rats and collected in about 1.5 ml micro centrifuging tubes.
2. The serum is separated within about 30 min. by centrifugation at speed of about 7000 rpm for about 15 min at about 4° C.
3. The working solution is pre-warmed to about 300° C.
4. About 10 µl of serum sample is transferred to the tubes containing about 1 ml of working reagent.
5. The absorbance of the sample and standard is measured against blank at about 340 nm
6. The result is determined by using the following calculation:

Calculation: Factor=(Conc. of standard)/(ΔAbs of standard)

Conc. of blood urea nitrogen (mg/dL)=(ΔAbs of specimen)/(ΔAbs of standard)×Factor The creatinine in serum/urine is estimated by Autozyme creatinine Jaffe method as follows:

1. Blood is withdrawn from animals (rabbits, rats, mice) and the blood samples are collected in 1.5 ml micro centrifuging tubes.
2. Serum is separated within about 30 min. by centrifugation at speed of about 7000 rpm for about 15 min at about 4° C.
3. About 50 µl of sample (serum/urine) is transferred to working reagent tubes.
4. Absorbance of sample (AS) or standard (Astd) at about 492 nm is measured using spectrophotometer.

The result is determined as follows:
Calculation:

ΔAbsorbance (Abs.)=Abs. at 90 sec.−Abs. at 30 sec.

Serum creatinine (mg/dL)=(ΔAbs of specimen)/(ΔAbs of standard)×2

Urine creatinine (mg/dL)=(ΔAbs of specimen)/(ΔAbs of standard)×2×dilution factor The procedure for estimating uric acid in serum is as follows:

1. Blood is withdrawn from the animal (rabbits, rats, mice) and the blood samples are collected in about 1.5 ml micro centrifuging tubes.
2. The serum is separated within about 30 min. by centrifugation at speed of about 7000 rpm for about 15 min at about 4° C.
3. About 25 μl of the serum sample is transferred to the working reagent tubes containing about 1 ml of reagent.
4. The mixture is incubated for about 5 minutes at about 37° C. for about 10 min. at room temperature.
5. After completion of the incubation, absorbance of the assay mixture against blank is measured at about 510 nm.

The result is determined as follows:

Calculation: Conc. of uric acid in serum (mg/dL)=
(Abs of specimen)/(Abs of standard)×6

The effect of the instant composition on 24-h blood urea nitrogen, serum creatinine and serum uric acid level for a period of about 28 days is studied as indicated in Example 2 above. The results obtained are tabulated in Table 5 wherein n=6; the data is represented as mean±SEM. (n=6), Data was analyzed by separate One-Way ANOVA followed by Dunnett's test for each parameter. $^{\#\#\#}$p<0.001 as compared with Normal group,  p<0.01, *p<0.001 as compared with (EG+AC).

TABLE 5

Effect of Instant composition on 24-h Blood Urea Nitrogen (BUN), serum creatinine and serum uric acid level

| Treatment | Day-28 | | | |
|---|---|---|---|---|
| | Normal Control | Disease Control | Ethylene Glycol + Instant composition (about 30 mg/kg) Treatment initiated on Day 15 | Ethylene Glycol + Instant composition (about 60 mg/kg) Treatment initiated on Day 15 |
| Blood Urea Nitrogen (mg %) | 8.07 ± 0.42 | 21.88 ± 0.71$^{\#\#\#}$ | 21.88 ± 1.14 | 17.51 ± 0.66*** |
| Serum Creatinine (mg %) | 1.31 ± 0.15 | 3.32 ± 0.60$^{\#\#\#}$ | 3.10 ± 0.08 | 1.92 ± 0.95*** |
| Serum Uric Acid (mg %) | 3.37 ± 0.42 | 8.13 ± 0.73$^{\#\#\#}$ | 7.27 ± 0.73 | 6.37 ± 1.42** |

As shown in Table 5, there is significant increase in 24-h BUN level in the disease control group when compared to the normal control group on day 28. The instant composition (about 60 mg/kg) significantly reversed BUN increment as compared to disease control group on day 28 as seen in Table 5.

As shown in Table 5, there is significant increase in 24-h serum Creatinine level in the disease control group when compared to the normal control group on day 28. The instant composition (about 60 mg/kg) significantly reversed serum Creatinine increment as compared to disease control group on day 28 as seen in Table 5.

As shown in Table 5, there is significant increase in 24-h serum uric acid level in the disease control group when compared to the normal control group on day 28. The instant composition (about 60 mg/kg) significantly reversed serum uric acid increment as compared to disease control group on day 28 as seen in Table 5. The instant composition shows enhancement of renal function leading to prevention of kidney failure.

Example 2.6

Hyperuricosuria is defined as urinary excretion of uric acid in excess. This is associated with the cellular destruction of renal tissue leading to marked kidney damage. Higher excretion of uric acid tends to acidify the urine, making it more susceptible for crystal stone formation.

The procedure for estimating uric acid in urine is estimated as follows:

1. Urine samples are collected from the metabolic cages in which the animals are placed.
2) About 25 μl of urine sample is transferred to the working reagent tubes containing about 1 ml of reagent (i.e. the Accurex Autozyme).
3) The mixture is incubated for about 5-10 minutes at about 37° C. at room temperature.
4) After completion of the incubation, absorbance of the assay mixture is measured against blank at about 510 nm.

The result is determined as follows:

Calculation: Conc. of uric acid in urine sample (mg/
dL)=(Abs of specimen)/(Abs of standard)×6

The effect of the instant composition on 24-h uric acid level for a period of about 28 days is studied as indicated in Example 2 above. The results obtained are tabulated in Table 6 wherein n=6; the data is represented as mean±SEM. (n=6), Data was analyzed by separate One-Way ANOVA followed by Dunnett's test for each parameter. $^{\#\#\#}$p<0.001 as compared with Normal group,  p<0.01, *p<0.001 as compared with (EG+AC).

TABLE 6

Effect of Instant composition on 24-h urine uric acid level

Urine Uric Acid (mg %)

| Treatment | Normal Control | Disease Control | Instant composition (about 30 mg/kg) Treatment initiated on Day 15 | Instant composition (about 60 mg/kg) Treatment initiated on Day 15 |
|---|---|---|---|---|
| Baseline | 0.92 ± 0.04 | 0.88 ± 0.02 | 0.85 ± 0.01 | 0.87 ± 0.01 |
| Day 14 | 0.91 ± 0.01 | 1.35 ± 0.05### | 1.57 ± 0.02*** | 1.55 ± 0.02*** |
| Day 21 | 0.93 ± 0.03 | 1.68 ± 0.04### | 1.51 ± 0.03** | t1.28 ± 0.02*** |
| Day 28 | 0.91 ± 0.02 | 1.87 ± 0.02### | 1.53 ± 0.009*** | t1.12 ± 0.06*** |

As shown in Table 6, there is significant increase in 24-h urine uric acid level in the disease control group when compared to the normal control group on day 14. The instant composition (about 60 mg/kg) significantly reversed urine uric acid increment as compared to disease control group on day 21 and onwards as seen in Table 6. The instant composition prevents further increase in urine uric acid and thus helps to reduce the chances of crystal stone formation. This shows that the instant composition prevents acidification of urine and helps in preventing recurrence of crystal stone formation. This aspect helps in managing urolithiasis and other related urological disorders.

Example 2.7

Formation of oxalate crystals causes acidification of urine which is associated with significant reduction in the pH of the urine. Low urinary pH is the important factor in nephrolithiasis. Uric acid, cystine, and calcium oxalate stones tend to form in acidic urine, whereas struvite (magnesium ammonium phosphate) and calcium phosphate stones form in alkaline urine. Hence, it is necessary to control urinary pH after one attack of kidney stone.

The effect of the instant composition on 24-h urine pH for a period of about 28 days is studied as indicated in Example 2 above. The results obtained are tabulated in Table 7 wherein n=6; the data is represented as mean±SEM. (n=6), Data was analyzed by separate One-Way ANOVA followed by Dunnett's test for each parameter. ####p<0.001 as compared with Normal group,  p<0.01, * p<0.001 as compared with (EG+AC).

As shown in Table 7, there is significant decrease in 24-h urine pH in the disease control group when compared to the normal control group on day 14. The instant composition (about 60 mg/kg) significantly reversed urine pH decline as compared to disease control group on day 21 and onwards as seen in Table 7. The instant composition controls urine pH decline and helps to prevent further recurrence of uric acid, cysteine, and calcium oxalate crystals. This aspect helps in managing urolithiasis and related urological disorders.

Example 2.8

Magnesium is a well-known inhibitor of calcium phosphate and calcium oxalate crystal growth. At physiological concentrations of oxalate, magnesium decreases both nucleation and growth rates. This is associated with the complex formation between magnesium and oxalate which increases the solubility product of calcium oxalate crystals. Hence it is necessary to maintain urine magnesium level.

Magnesium in urine is estimated by the following procedure:
1. About one milliliter of urine is diluted with about 5 ml distilled water.
2. Proteins are precipitated by the addition of about 2 ml of about 10% sodium tungstate and about 2 ml of about 0.67 N $H_2SO_4$, and the mixture is centrifuged for about five minutes at about 2,500 rpm.
3. To about 5 ml of the supernatant, about 1 ml of distilled water, about 1 ml 0.1% polyvinyl alcohol solution, about 1 ml of about 0.05% titan yellow solution and about 2 ml of about 4 N NaOH solution are added.

TABLE 7

Effect of Instant composition on 24-h urine pH 24-h Urine pH

| Treatment | Normal Control | Disease Control | Ethylene Glycol + Instant composition (about 30 mg/kg) Treatment initiated on Day 15 | Ethylene Glycol + Instant composition (about 60 mg/kg) Treatment initiated on Day 15 |
|---|---|---|---|---|
| Baseline | 7.13 ± 0.04 | 7.2 ± 0.02 | 7.16 ± 0.04 | 7.03 ± 0.07 |
| Day 14 | 7.1 ± 0.06 | 6.63 ± 0.13#### | 6.75 ± 0.05 | 6.65 ± 0.07 |
| Day 21 | 7.21 ± 0.06 | 6.2 ± 0.05#### | 6.75 ± 0.09*** | 6.98 ± 0.03*** |
| Day 28 | 7.18 ± 0.07 | 6.28 ± 0.12#### | t6.68 ± 0.12** | 7.05 ± 0.04*** |

4. A blank using about 1 ml of $CaCl_2$ solution in place of urine is treated similarly to the test.
5. For standard reading, about 2.5 ml of the working Mg standard containing about 12.5 µg of magnesium is made to about 5 ml and treated as the test protein-free supernatant, replacing the about 1 ml distilled water with about 1 ml of $CaCl_2$ solution.
6. The absorbance of the standard and unknown solution is read against blank at about 520 nm.

The result is determined as follows:

Calculation:

$$\text{mg of magnesium in 1 ml of urine} = \frac{\text{Absorbance of test}}{\text{Reading of standard}} \times \frac{0.0125}{0.5}$$

The effect of the instant composition on 24-h urine magnesium level for a period of about 28 days is studied as indicated in Example 2 above. The results obtained are tabulated in Table 8 wherein n=6; the data is represented as mean±SEM. (n=6), Data was analyzed by separate One-Way ANOVA followed by Dunnett's test for each parameter. ####$p<0.001$ as compared with Normal group,  $p<0.01$, *$p<0.001$ as compared with (EG+AC).

TABLE 8

Effect of Instant composition on 24-h urine magnesium level

| | Urine Magnesium (mg/ml) | | | |
|---|---|---|---|---|
| Treatment | Normal Control | Disease Control | Ethylene Glycol + Instant composition (30 mg/kg) Treatment initiated on Day 15 | Ethylene Glycol + Instant composition (60 mg/kg) Treatment initiated on Day 15 |
| Baseline | 0.022 ± 0.0009 | 0.023 ± 0.0004 | 0.021 ± 0.0003 | 0.02 ± 0.0002 |
| Day-14 | 0.023 ± 0.001 | 0.006 ± 0.0004#### | 0.0060 ± 0.0004 | 0.006 ± 0.0009 |
| Day-21 | 0.023 ± 0.0004 | 0.004 ± 0.0001#### | 0.005 ± 0.0003 | 0.007 ± 0.0002 |
| Day-28 | 0.023 ± 0.0005 | 0.004 ± 0.0002#### | 0.005 ± 0.0003 | 0.009 ± 0.0009** |

As shown in Table 8, there is significant decrease in 24-h urine magnesium level in the disease control group when compared to the normal control group on day 14. The instant composition (about 60 mg/kg) significantly protected urine magnesium decline as compared to disease control group on day 21 and onwards as seen in Table 8. The instant composition helps in inhibition of nucleation and crystal growth against renal calculi. This aspect helps in managing urolithiasis and related urological disorders.

Example 3

Histological Evaluation

The urolithiasis induced animals are sacrificed after 28th day. Kidneys are removed for histological study. For light microscopy, the rat kidney slices are stained with hematoxylin and eosin reagent.

Figure 1:
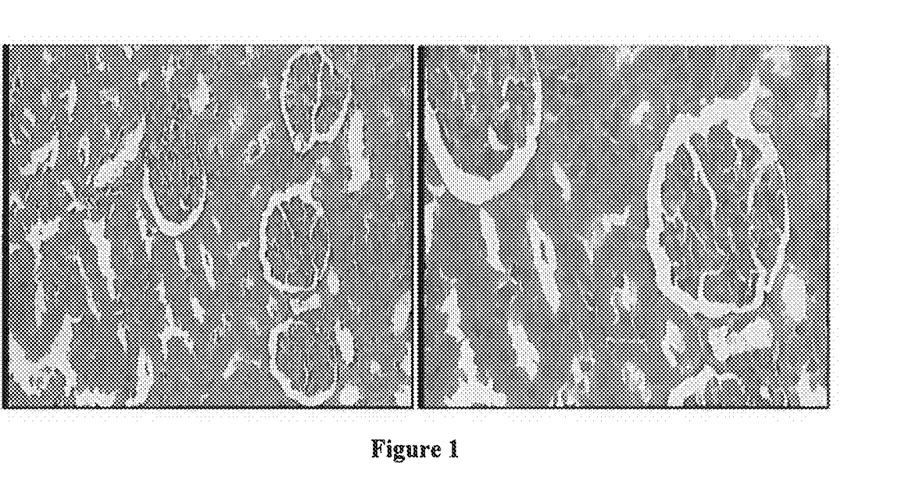
FIG. 1 shows Kidney section of normal rats showing normal cellular structure (H and E×200 i.e. kidney stained progressively with Hematoxylin and Eosin Y at 200× magnification), (H and E×400 i.e. kidney stained progressively with Hematoxylin and Eosin Y at 400× magnification).

Histopathological Observations:

The histopathological observations of kidney of normal rats showed normal structure and architectural intactness without any apparent damages (FIG. 1).

Figure 2:
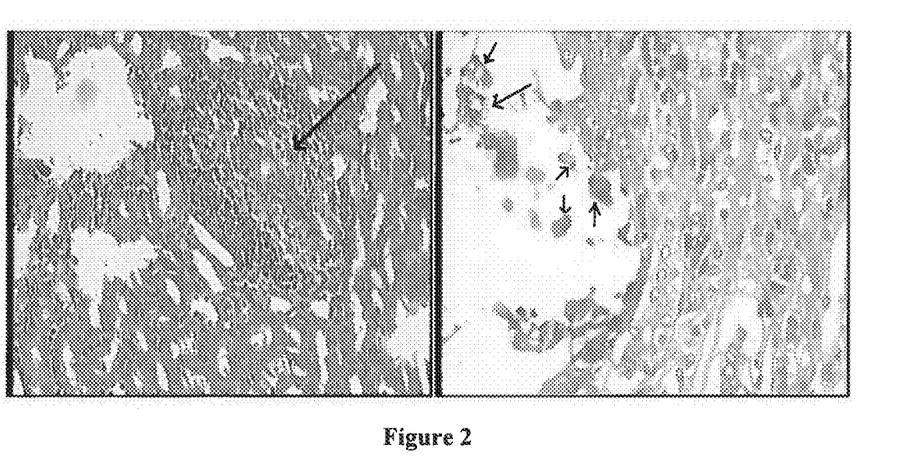
FIG. 2 shows kidney section of EG+AC (ethylene glycol+ ammonium chloride) treated rats, showing calcium oxalate crystals inside the tubules, dilation of the proximal tubule along with interstitial inflammation (H and E×400).

Kidney of ethylene glycol induced urolithic rats showed marked interstitial inflammation of lymphocytes and monocytes. Also interstitial fibrosis and cloudy change in tubular epithelial cells is seen. Intra-tubular casts and exfoliated epithelial cells are also seen. More number of crystals is seen in the disease control group (FIG. 2).

Figure 3:
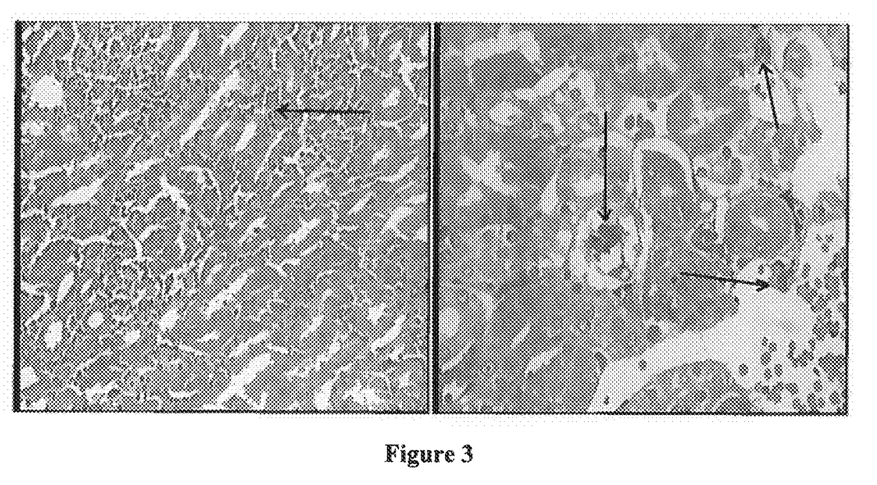
FIG. 3 shows kidney section of rats treated with EG (0.75%)+AC (1%) for about 3 days and only ethylene Glycol (0.75%) until about day 28 and treated with the instant composition (about 60 mg/kg comprising 35% Trigonelline & 18% 4-Hydroxyisoleucine amino acid) from day 15 onwards, showing mild interstitial inflammation of lymphocytes and mild cloudy change in tubular epithelial cells with few crystals.

Rats treated with administration of instant composition (about 60 mg/kg) showed minimal number of crystals and minimal damage, mild interstitial inflammation of lymphocytes and mild cloudy change in tubular epithelial cells are also seen in this group (FIG. 3).

The instant composition shows prevention of kidney tissue damage as it reduces interstitial inflammation and fibrosis and inhibition of crystal growth against renal calculi showing complete removal of more number of kidney stones compared to disease control group.

Example 4

Effect of Instant Composition in Patients Suffering from Urolithiasis

A study to assess the efficacy of the instant composition in patients diagnosed with renal calculi is conducted. In this study, two patients suffering from unilateral renal calculi with symptoms of acute renal colic, muscular distension and blood in urine are given tablets of instant composition. Patient 1 is having about 57 kg of body weight while patient 2 is of about 78 kg body weight. Abdomen Ultrasound Scanning is conducted before initiating the treatment and after completion of treatment. The patient 1 is diagnosed with the presence of right renal mild obstructive changes due to about 6.3 mm right UV junction calculus with edema and bilateral renal calyceal calculi of about 2-3 mm. The report is presented in Table 10.

TABLE 10

Ultrasound Scanning report of Patient 1 prior treatment
USG: ABDOMEN & PELVIS

Liver is normal in size, shape and shows normal echopattern. No focal lesion seen.
Intrahepatic biliary radical and portal vein radicals appear normal. CBD appears normal.
Gall bladder is well distended with normal wall thickness.
Pancreas appears normal in size, shape and echopattern. No focal lesion seen.
Spleen is normal in size, shape & echopattern. No focal lesion seen.
Right Kidney: 99 × 43 mm.      Left Kidney: 98 × 42 mm.
Both kidney appears normal in size, shape, position & echopattern with maintained C-M differentiation.
Right kidney shows mild obstructive changes due to 6.3 mms right UV junction calculus with edema.
Both kidney shows calyceal calculi of about 2-3 mms.
Urinary bladder is well distended & shows normal wall with clear contents.
Prostate is normal in size, shape and echopattern. No focal lesion seen.

TABLE 10-continued

Ultrasound Scanning report of Patient 1 prior treatment
USG: ABDOMEN & PELVIS

No e/o free fluid in abdomen or pelvis. No e/o abdomino-pelvic lymphadenopathy.
No abnormal bowel dilatation is seen.
CONCLUSION:
 Right renal mild obstructive changes due to 6.3 mms right UV junction calculus with edema.
 Bilateral renal calyceal calculi of about 2-3 mms.

The patient 2 is diagnosed with the presence of about 3.8 mm calculus in right kidney. The report is presented in Table 11.

TABLE 11

Ultrasound Scanning report of Patient 2 prior treatment

Cli.profile - Lower chest pain. No bowel or urinary complaints.
Ultrasound Abdomen Liver is normal in size - shows normal echotexture. No focal parenchymal pathology seen. IHBR not dilated. PV & CBD are WNL.
Gall bladder is well distended & has smooth outlines. No obvious calculus seen.
Spleen is normal in size & echogenicity.
Pancreas is normal.
Both kidneys are normal in size and echogenicity. Normal cortical thickness. A 3.8 mm calculus is seen in the lower pole of right kidney. No HN seen. No calculus or HN seen on left side.
Aorta, IVC and para-aortic areas are clear. No obvious LNpathy.
No ascites.
Urinary bladder is well distended. UV junctions are clear. No calculus or any intrinsic bladder pathology seen.
* No probe tenderness at present.
Impression - 3.8 mm calculus in right kidney. Otherwise, Within normal limits.

The two patients are given a tablet twice daily containing about 300 mg of the instant composition. With continuous treatment of the patients with the instant composition, Abdomen Ultrasound Scanning is conducted again. The patient 1 showed complete removal of calculi within about 27 days of continuous treatment and the patient 2 showed complete removal of calculi within about 38 days of continuous treatment. The reports are presented in Tables 12 and 13 for patients 1 and 2, respectively.

TABLE 12

Ultrasound Scanning report of Patient 1 after completion of treatment

REAL TIME B-MODE USG OF WHOLE ABDOMEN WAS DONE:
Liver is normal in size, shape and shows normal parenchymal echopattern. No focal or diffuse parenchymal abnormality is noted. HBR & IHPR appear normal. Portal vein and Common bile duct are normal in course and caliber.
Gall Bladder is optimally distended and appear normal with normal wall thickness. No obvious mobile calculus or mass lesion seen.
Pancreas appears normal in size, shape and echo pattern. No focal lesion seen.
Spleen appears normal in size, shape and echo pattern. No focal lesion seen.
Right Kidney appears normal in size, shape and echo pattern with maintained C-M differenciation. No obvious renal calculus or hydronephrosis.
Left Kidney appears normal in size, shape and echo pattern with maintained C-M differenciation. No obvious renal calculus or hydronephrosis.
Urinary Bladder is optimally distended and appear normal with normal wall thickness. No obvious mobile vesical calculus or mass lesion seen.

TABLE 12-continued

Ultrasound Scanning report of Patient 1 after completion of treatment

Prostate appears normal in size, shape and echo pattern. No focal lesion seen.
No obvious free fluid or lymphadenopathy is noted in the abdomen.
CONCLUSION Abdominal sonography is within normal limits
Suggested clinic-pathological correlation

TABLE 13

Ultrasound Scanning report of Patient 2 after completion of treatment
Cli. profile - No bowel or urinary complaints
Ultrasound Abdomen Liver is normal in size - shows normal echotexture. No focal parenchymal pathology seen. IHBR not dilated. PV & CBD are WNL.
Gall bladder is well distended & has smooth outlines. No calculus seen.
Spleen is normal in size & echogenicity.
Pancreas is normal. No focal lesion seen. MPD is not dilated. Peri-pancreatic fat planes are preserved.
Both kidneys are normal in size & echogenicity. No obvious calculus or hydronephrosis seen on both sides.
Aorta, IVC and para-aortic areas are clear. No obvious LNpathy.
No ascites.
Urinary bladder is well distended. UV junctions are clear. No obvious calculus or any intrinsic bladder pathology seen. Residual urine is not significant.
Prostate is normal in size & echogenicity.
No probe tenderness in the RIF at present. No free fluid in cul de sac.
Impression - Normal study.

TABLE 14

Ultrasound Scanning report of Patient 2 after discontinuing treatment

FINDINGS:-
Liver is normal in size, shape and echopattern. No evidence of focal lesion seen.
Portal and hepatic venous confluence are normal. No IHBR dilatation seen.
Gall bladder is well distended and normal. No calculus or mass seen.
CBD is normal in caliber.
Pancreas is normal in size and echopattern. No focal lesion seen.
Spleen is normal in size with homogenous ethopattern. No focal lesion seen.
Both kidneys are homogenous in echopattern. No hydronephrosis seen on both sides.
Both ureters are not dilated.
Urinary Bladder is well distended shows normal wall thickness. No mass or calculus seen.
Prostate is normal in size and echopattern.
Aorta, IVC and retroperitoneum is normal.
No obvious bowel dilatation is seen. No abnormal bowel wall thickening is seen.
IMPRESSION:- No abnormality detected The two patients showed no relapse of stone formation for a period of about 8 months after discontinuing the treatment (Table 14).

TABLE 15

Analysis of removal of renal calculi using ultrasound of abdomen and pelvis

| | Kidney and Bladder | |
| --- | --- | --- |
| | Before Treatment with Instant Composition | After Treatment with Instant Composition |
| Patient 1 | Right renal mild obstructive changes due to about 6.3 mm right UV junction calculus with edema | No calculus |

TABLE 15-continued

Analysis of removal of renal calculi using ultrasound of abdomen and pelvis

| | Kidney and Bladder | |
|---|---|---|
| | Before Treatment with Instant Composition | After Treatment with Instant Composition |
| Patient 2 | About 3.8 mm calculus in right kidney | No calculus |

The treatment showed complete removal of calculi with all normal results for liver, kidney, spleen, gall bladder and urinary bladder indicating the effect of the instant composition against urolithiasis.

Example 5

Effect of Instant Composition in Patients Suffering from Ureterolithiasis

A study to assess the efficacy of the instant composition in patients diagnosed with ureteric calculi is conducted. In this study, a patient (i.e. patient 3) diagnosed with ureteric calculus and hydronephrosis is given tablets of instant composition. The Patient 1 is having about 72 kg of body weight. Abdomen Ultrasound Scanning is conducted before initiating the treatment and after completion of treatment. The reports are presented in Table 16 and 17.

TABLE 16

Ultrasound Scanning report of Patient 3 prior to treatment

USG K.U.B.
RIGHT KIDNEY - 10.5 × 4.5 cm in size, normal in size/shape/ echogenicity. No E/o hydronephrosis/hydroureter/calculus
LEFT KIDNEY - 10.5 × 4.5 cm in size, normal in size/shape/echogenicity.
c/o mild hydronephrosis with hydroureter due to 10 mm size terminal ureteric calculus
URINARY BLADDER - Distended normal
IMPRESSION - Left terminal ureteric calculus, causing mild hydronephrosis with hydroureter

TABLE 17

Ultrasound Scanning report of Patient 3 after completion of treatment

Exam ULTRASONOGRAPHY OF THE URINARY TRACT.
Report
Real time ultrasonography of the urinary tract was performed.
Both kidneys are normal in size, shape, position, & echotexture.
There is no e/o hydronephrosis, calculus or mass in either kidney. The cortical thickness is well maintained in both kidneys.
The right kidney measures 10.6 × 3.9 cms.
The left kidney measures 10.2 × 4.5 cms.
The urinary bladder is well distended with normal walls. No calculus or mass is seen in the bladder
The prostate is normal in size & echotexture measuring
2.7 × 2.7 × 2.6 cms
Its weight is 10 gms
OPINION: Normal findings on the Ultrasonography of the Urinary Tract.

The treatment showed complete removal of ureteric calculi indicating the effect of the instant composition against ureterolithiasis.

We claim:

1. A method of managing urolithiasis and related urological disorders, said method comprising act of administering composition consisting of trigonelline or its derivative(s) and 4-hydroxyisoleucine or its derivative(s), optionally along with pharmaceutical excipient, to subject in need thereof.

2. The method as claimed in claim 1, wherein the urolithiasis is selected from a group comprising nephrolithiasis, ureterolithiasis and cystolithiasis or any combination thereof.

3. The method as claimed in claim 1, wherein the related urological disorder is selected from a group comprising hyperoxaluria, hypocitraturia, hyperuricosuria, accumulation of calcium crystals in renal tubule, low creatinine clearance rate, high BUN, serum creatinine and serum uric acid level, low urinary pH, recurrence of calculi and other kidney disorder or any combination thereof.

4. The method as claimed in claim 1, wherein the trigonelline or its derivative(s) is at concentration ranging from about 30% w/w to about 90% w/w; the 4-hydroxyisoleucine or its derivative(s) is at concentration ranging from about 10% w/w to about 30% w/w; and the pharmaceutical excipient is at concentration ranging from about 0.5% w/w to about 30% w/w.

5. The method as claimed in claim 1, wherein the derivative(s) of trigonelline is selected from group comprising hydrochloride derivatives, acetate derivatives, citrate derivatives, benzoate derivatives, salt derivatives and acid derivatives, preferably hydrochloride derivatives.

6. The method as claimed in claim 1, wherein the derivative(s) of 4-hydroxyisoleucine is selected from group comprising hydrochloride derivatives, acetate derivatives, citrate derivatives, benzoate derivatives, salt derivatives and acid derivatives, preferably hydrochloride derivatives.

7. The method as claimed in claim 1, wherein the pharmaceutical excipient is selected from group comprising gums, granulating agents, binders, lubricants, disintegrating agents, sweetening agents, additives, solvents, glidants, anti-adherents, anti-static agents, surfactants, anti-oxidants, viscosity enhancers, plant cellulosic material, coloring agents, flavoring agents, coating agents, plasticizers, preservatives, suspending agents, emulsifying agents and spheronization agents or any combination thereof.

8. The method as claimed in claim 1, wherein the composition is formulated into dosage forms selected from group comprising solid oral formulation, liquid oral formulation, parenteral formulation, phytoceutical, nutraceutical and food stuff or any combinations thereof.

9. The method as claimed in claim 1, wherein the composition is administered at dose ranging from about 1 mg/kg to about 100 mg/kg, preferably ranging from about 1 mg/kg to about 25 mg/kg of body weight of said subject per day.

10. The method as claimed in claim 1, wherein the subject is a mammal, including human being.

* * * * *